(12) United States Patent
Miyamoto et al.

(10) Patent No.: US 10,780,204 B2
(45) Date of Patent: Sep. 22, 2020

(54) BIOLOGICAL FLUID-TREATING FILTER AND FILTER DEVICE

(71) Applicant: ASAHI KASEI MEDICAL CO., LTD., Tokyo (JP)

(72) Inventors: Daisuke Miyamoto, Tokyo (JP); Satoru Inoue, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 566 days.

(21) Appl. No.: 15/514,969

(22) PCT Filed: Sep. 30, 2015

(86) PCT No.: PCT/JP2015/077742
§ 371 (c)(1),
(2) Date: Mar. 28, 2017

(87) PCT Pub. No.: WO2016/052618
PCT Pub. Date: Apr. 7, 2016

(65) Prior Publication Data
US 2017/0216504 A1    Aug. 3, 2017

(30) Foreign Application Priority Data
Oct. 2, 2014    (JP) .................... 2014-204189

(51) Int. Cl.
*A61M 1/02* (2006.01)
*B01D 39/16* (2006.01)
(Continued)

(52) U.S. Cl.
CPC .............. *A61M 1/029* (2013.01); *A61M 1/02* (2013.01); *A61M 1/34* (2013.01); *A61M 1/3406* (2014.02);
(Continued)

(58) Field of Classification Search
CPC ............... B01D 39/1623; B01D 39/16; B01D 2239/04; B01D 2239/1233;
(Continued)

(56) References Cited

U.S. PATENT DOCUMENTS 5,648,442 A * 7/1997 Bowers ................... C07F 9/091
427/372.2
6,225,431 B1 * 5/2001 Jones ...................... C07F 9/091
427/384
(Continued)

FOREIGN PATENT DOCUMENTS

JP    H08-281100 A    10/1996
JP    3030086 B2    4/2000
(Continued)

OTHER PUBLICATIONS

Supplemental European Search Report for European Application No. 15847778.6 dated Sep. 13, 2017.
(Continued)

*Primary Examiner* — Krishnan S Menon
*Assistant Examiner* — Waqaas Ali
(74) *Attorney, Agent, or Firm* — Greenblum & Bernstein, P.L.C.

(57) ABSTRACT

Provided is a biological fluid-treating filter for treating a biological fluid containing erythrocytes, which has a matrix and a polymer retained by the matrix, the polymer having a zwitterion-containing functional group and a basic nitrogen-containing functional group. By using the filter in which the polymer has the zwitterion-containing functional group and the basic nitrogen-containing functional group, it is possible to treat the biological fluid containing erythrocytes without adversely affecting the erythrocytes.

8 Claims, 5 Drawing Sheets

(51) Int. Cl.

| | | |
|---|---|---|
| *C08L 101/00* | (2006.01) | |
| *A61M 1/34* | (2006.01) | |
| *C08L 33/14* | (2006.01) | |
| *C08L 67/02* | (2006.01) | |
| *A61M 1/36* | (2006.01) | |
| *D06M 15/267* | (2006.01) | |
| *A61K 35/14* | (2015.01) | |
| *D06M 101/32* | (2006.01) | |

(52) U.S. Cl.
CPC ............... *A61M 1/36* (2013.01); *B01D 39/16* (2013.01); *B01D 39/1623* (2013.01); *C08L 33/14* (2013.01); *C08L 67/02* (2013.01); *C08L 101/00* (2013.01); *D06M 15/267* (2013.01); *A61K 35/14* (2013.01); *B01D 2239/04* (2013.01); *B01D 2239/0478* (2013.01); *B01D 2239/1233* (2013.01); *D06M 2101/32* (2013.01)

(58) Field of Classification Search
CPC .......... B01D 2239/0478; A61M 1/029; A61M 1/3406; A61M 1/36; A61M 1/02; A61M 1/34; D06M 15/267; D06M 2101/32; C08L 101/00; C08L 67/02; C08L 33/14; A61K 35/14
See application file for complete search history.

(56) References Cited

U.S. PATENT DOCUMENTS

| | | | |
|---|---|---|---|
| 6,251,276 B1 | 6/2001 | Motomura | |
| 9,186,441 B2 | 11/2015 | Ochiai et al. | |
| 2003/0171443 A1* | 9/2003 | Erbacher | ................. B01J 41/14 521/27 |
| 2004/0253204 A1 | 12/2004 | Yagi et al. | |
| 2008/0190842 A1 | 8/2008 | Mizomoto et al. | |
| 2008/0190843 A1 | 8/2008 | Mizomoto et al. | |
| 2008/0262181 A1 | 10/2008 | Kitano et al. | |
| 2012/0024779 A1* | 2/2012 | Ochiai | ................. A61L 33/064 210/506 |
| 2012/0067821 A1 | 3/2012 | Chang et al. | |

FOREIGN PATENT DOCUMENTS

| | | |
|---|---|---|
| JP | 2000-197814 A | 7/2000 |
| JP | 4252449 B2 | 1/2009 |
| JP | 4295359 B2 | 7/2009 |
| JP | 2011-504526 A | 2/2011 |
| WO | 1993/001221 A1 | 1/1993 |
| WO | 1998/022516 A1 | 5/1998 |
| WO | 2005/113620 A1 | 12/2005 |
| WO | 2006/016163 A1 | 2/2006 |
| WO | 2006/016166 A1 | 2/2006 |
| WO | 2009/067562 A1 | 5/2009 |
| WO | 2010/113632 A1 | 10/2010 |

OTHER PUBLICATIONS

International Search Report issued in International Application No. PCT/JP2015/077742, dated Jan. 12, 2016.
International Preliminary Report on Patentability in International Application No. PCT/JP2015/077742, dated Apr. 4, 2017.

* cited by examiner

Fig. 4

| | EXAMPLE | | | | | | | | | | |
|---|---|---|---|---|---|---|---|---|---|---|---|
| | 1 | 2 | 3 | 4 | 5 | 6 | 7 | 8 | 9 | 10 | 11 |
| MEMA (mol%) | 70 | 70 | 70 | 70 | 95 | 95 | 67.5 | 67.5 | MMA: 67.5 | MMA: 67.5 | MMA: 67.5 |
| DEAEMA (mol%) | 10 | 10 | 10 | 10 | 2.5 | 2.5 | 30 | 2.5 | DEAEA: 30 | DEAEA: 30 | DEAEA: 30 |
| CMB (mol%) | 20 | 20 | 20 | 20 | 2.5 | 2.5 | 2.5 | 30 | 2.5 | SMB: 2.5 | PMB: 2.5 |
| COAT AMOUNT (mg/gMW) | 20 | 2.5 | 30 | 20 | 1.0 | 2.5 | 35 | 1.0 | 20 | 20 | 20 |
| MATRIX MATERIAL | POLYETHYLENE TEREPHTHALATE (PET) | | | POLYBUTYLENE TEREPHTHALATE (PBT) | POLYETHYLENE TEREPHTHALATE (PET) | | | | | | |
| HEMOLYSIS | (-) | (-) | (-) | (-) | (-) | (-) | (-) | (-) | (-) | (-) | (-) |
| LEUKOCYTE REMOVAL CAPACITY (-log) | 4.5 | 4.4 | 4.5 | 4.5 | 4.4 | 4.4 | 4.5 | 4.3 | - | - | - |
| PLATELET REMOVAL CAPACITY (%) | 99 | 99 | 99 | 99 | 99 | 99 | 99 | 99 | - | - | - |

Fig. 5

| | COMPARATIVE EXAMPLE | | | | | | | | | | REFERENCE EXAMPLE |
|---|---|---|---|---|---|---|---|---|---|---|---|
| | 1 | 2 | 3 | 4 | 5 | 6 | 7 | 8 | 9 | 10 | 1 |
| MEMA (mol%) | 70 | 85 | 85 | 30 | MEMA: 60 | MEMA: 70 | MEMA: 60 | MEMA: 70 | MEMA: 70 | MEMA: 67.5 | SEPACEL FILTER FROM ASAHI KASEI MEDICAL |
| DEAEMA (mol%) | 30 | 15 | - | 35 | DEAEMA: 30 | DEAEMA: 30 | DEAEMA: 30 | DEAEMA: 30 | DEACMA: 30 | DEACMA: 2.5 | |
| CMB (mol%) | - | - | 15 | 35 | AH: 10 | AH: 20 | DEG: 10 | DEG: 20 | CMB: 20 | CMB: 30 | |
| COAT AMOUNT (mg/gMW) | 5 | 20 | 20 | 20 | 20 | 20 | 20 | 20 | 30 | 1.0 | |
| MATRIX MATERIAL | POLYETHYLENE TEREPHTHALATE (PET) | | | | | | | | | | |
| HEMOLYSIS | (+) | (-) | (-) | (±) | (+) | (-) | (+) | (-) | (+) | (+) | (-) |
| LEUKOCYTE REMOVAL CAPACITY (-log) | 4.0 | 2.8 | 2.5 | 3.5 | 3.7 | 3.2 | 3.7 | 3.1 | 4.4 | 4.3 | 3.0 |
| PLATELET REMOVAL CAPACITY (%) | 99 | 75 | 60 | 99 | 90 | 90 | 99 | 99 | 99 | 99 | 95 |

BIOLOGICAL FLUID-TREATING FILTER AND FILTER DEVICE

TECHNICAL FIELD

The present invention relates to a filter and a filter device for treating a biological fluid containing erythrocytes. This application claims priority to Japanese Patent Application No. 2014-204189, filed Oct. 2, 2014 and all the disclosure described in the Japanese application is hereby incorporated by reference.

BACKGROUND ART

In the field of blood transfusion, leukapheresis is generally carried out in which mixed leukocytes contained in a blood product are removed before transfusion. This is because side effects, such as headache, nausea, and chill, encountered in blood transfusion, and serious side effects, such as alloantigen sensitization, transfusion-associated graft-vs-host disease (GVHD), and virus infection, exerting a more serious influence on blood receivers have been shown to be caused mainly due to leukocytes mixed in the blood product used for the blood transfusion.

Also for platelets, an anti-platelet antibody has been shown to be formed in the body of recipients of blood transfusion, and the demand for a blood product from which platelets have been removed keeps on rising for suppression of formation of the anti-platelet antibody.

Also in the field of blood purification, attention has been given to leukocytapheresis therapy which treats inflammatory conditions including septicemia and systemic inflammatory response syndrome (SIRS) by removing leukocytes from patients with the inflammatory conditions using an extracorporeal circulation filter device to suppress the production of physiologically active substances such as cytokines and alarmins.

The filter for treating these biological fluids containing erythrocytes, such as blood and a blood product, requires the ability to remove targeted materials as well as having no adverse effects, such as hemolysis, on erythrocytes.

For a filter for removing leukocytes and platelets from a biological fluid containing erythrocytes, Patent Literature 1 discloses a filter and a filter device in which interactions with both leukocytes and platelets can be increased to efficiently remove both of them by coating the matrix surface with a polymer containing an alkylsulfonate of a quaternary amine to cationize and hydrophilize the surface.

Patent Literature 2 discloses a filter and a filter device which remove leukocytes and platelets and are excellent in the blood priming properties by the coating of the matrix surface with a polymer containing a basic monomer, such as methyl (meth)acrylate and dimethylaminoethyl acrylate, and a protic neutral hydrophilic monomer, such as 2-hydroxyethyl (meth)acrylate. Patent Literature 3 discloses a technique which involves enhancing the leukocyte removal performance by the surface into which both a basic functional group and an acidic functional group are introduced using separate monomers.

Patent Literature 4 discloses a technique which involves making the leukocyte removal performance compatible with the hemolysis prevention properties by coating the matrix surface with a ternary polymer in which the effect of a cationic monomer is reduced to suppress damage on erythrocytes due to the cationicity of the polymer and a nonionic monomer is added for the polymer composition to prevent hemolysis.

In accordance with the same concept, Patent Literature 5 discloses a technique which involves making the leukocyte removal capacity compatible with the hemolysis prevention properties by coating the matrix surface with a ternary polymer in which a monomer having an acidic functional group in the side chain is added for the polymer composition.

Patent Literature 6 discloses a technique which involves enhancing the blood compatibility of a material by introducing a functional group having a zwitterion and a functional group permanently having a cation, such as a quaternary amine, into the substance surface contacting with blood to delay the surface adhesion of blood cells and plasma proteins in the blood as well as coating the surface with heparin contained as an anticoagulating agent in the blood.

CITATION LIST

Patent Literature

Patent Literature 1: Japanese Patent Laid-Open No. 2000-197814
Patent Literature 2: Japanese Patent No. 4252449
Patent Literature 3: Japanese Patent Laid-Open No. 08-281100
Patent Literature 4: International Publication No. WO 2006/016163
Patent Literature 5: International Publication No. WO 2006/016166
Patent Literature 6: Japanese Patent No. 4295359

SUMMARY OF INVENTION

Technical Problem

An object of the present invention is to provide a filter and a filter device for treating a biological fluid, capable of treating a biological fluid containing erythrocytes without adversely affecting the erythrocytes.

Hydrophilicity was attempted to be enhanced to improve the wettability of the filter by coating the matrix surface with a polymer containing monomer units containing an alkylsulfonate of a quaternary amine for the technique disclosed in Patent Literature 1 and a polymer containing monomer units containing a basic nitrogen-containing functional group and monomer units containing a protic neutral hydrophilic group for the technique disclosed in Patent Literature 2, aiming at an enhancement in leukocyte removal performance and platelet removal performance. However, when the present inventors treated blood with the filters described in Patent Literatures 1 and 2, there were problems of erythrocyte adhesion to the filters and erythrocyte hemolysis.

Patent Literature 3 discloses a technique involving enhancing leukocyte removal performance using the surface into which both a basic functional group and an acidic functional group are introduced using separate monomers; however, it does not make mention as to erythrocyte hemolysis. Patent Literature 3 refers to, as a means, the use of a monomer as an amphoteric chemical species as a method for introducing a basic functional group and an acidic functional group; however, it does not discloses whether or not the use of the amphoteric chemical species can enhance leukocyte removal performance as with the case of the introduction of a basic functional group and an acidic functional group using separate monomers. The present inventors evaluated the surface into which ethyl betaine methacrylate, having both a basic functional group and an acidic functional group, was introduced, in this respect; as a result, no enhancement in leukocyte removal performance was observed.

The technique disclosed in Patent Literature 4 attempted to make the leukocyte removal capacity compatible with the hemolysis prevention properties by coating the matrix surface with the ternary polymer in which a nonionic monomer, such as MMA (methyl methacrylate) or DEGMEMA (diethylene glycol methoxyethyl methacrylate), was added as a third component of the polymer to reduce the anionicity of a basic nitrogen-containing functional group, resulting, however, in insufficient hemolysis prevention.

In accordance with the same concept as that in Patent Literature 4, the technique disclosed in Patent Literature 5 also attempted to make the leukocyte removal performance compatible with the hemolysis prevention properties by coating the matrix surface with the ternary polymer in which a monomer having a cationic functional group was added as a third component, again resulting, however, in insufficient hemolysis prevention.

Patent Literature 6 discloses a biocompatible polymer in which a zwitterionic group and a quaternary amine permanently having a cation are simultaneously introduced; however, it does not make mention as to the leukocyte removal performance of the surface into which the polymer was introduced and erythrocyte hemolysis. The present inventors evaluated the surface coated with a polymer containing a zwitterion-containing functional group and diethylammonium chloride methacrylate, having a quaternary amine, in this respect; as a result, the hemolysis was insufficiently prevented.

Solution to Problem

As a result of intensive studies for achieving the above object, the present inventors have found that a filter having a matrix retaining a polymer having a zwitterion-containing functional group and a basic nitrogen-containing functional group in the side chain can be used to treat an erythrocyte-containing biological fluid without adversely affecting the erythrocytes, thereby accomplishing the present invention.

Thus, aspects of the present invention relate to the following.

[1] A biological fluid-treating filter for treating a biological fluid containing erythrocytes, comprising a matrix and a polymer retained by the matrix, the polymer comprising a zwitterion-containing functional group and a basic nitrogen-containing functional group, wherein the basic nitrogen-containing functional group is $-NH_2-$, $-NHR_1$, or $-NR_2R_3$ where $R_1$, $R_2$, and $R_3$ are alkyl groups having one to three carbon atoms.

[2] The biological fluid-treating filter according to [1], wherein the polymer is retained in an amount of 1.0 mg or more per g of the matrix.

[3] The biological fluid-treating filter according to [1] or [2], wherein the zwitterion-containing functional group is derived from at least one selected from the group consisting of carbobetaine, sulfobetaine, and phosphobetaine.

[4] The biological fluid-treating filter according to any of [1] to [3], wherein the polymer further contains a nonionic group, and the molar proportions of monomer units having the nonionic group (l), monomer units having the basic nitrogen-containing functional group (m), and monomer units having the zwitterion-containing functional group (n) satisfy the relationships:

$$l+m+n=100,$$

$$0<l,m,n<100,$$

assuming that a total of molar proportions of the monomer units constituting the polymer is 100.

[5] The biological fluid-treating filter according to [4], wherein the molar proportion of monomer units having the nonionic group (l) to monomer units having the basic nitrogen-containing functional group (m) to monomer units having the zwitterion-containing functional group (n) is 1/m/n=40 to 97/1.5 to 32.5/1.5 to 32.5.

[6] The filter according to any of [3] to [5], wherein in the polymer, the monomer unit having the nonionic group is an alkoxyalkyl (meth)acrylate and the monomer unit having the basic nitrogen-containing functional group is an N,N-dialkylaminoalkyl (meth)acrylate.

[7] The filter according to [6], wherein the alkoxyalkyl (meth)acrylate is 2-methoxyethyl (meth)acrylate; the N,N-dialkylaminoalkyl (meth)acrylate is N,N-diethylaminoethyl (meth)acrylate; and the zwitterion-containing monomer is methyl betaine methacrylate.

[8] The filter according to any of [1] to [7], wherein the material of the matrix is polyethylene terephthalate or polybutylene terephthalate.

[9] The filter according to any of [1] to [6], wherein the matrix is a nonwoven fabric.

[10] A filter device for treating a biological fluid containing erythrocytes, comprising a housing comprising an inlet and an outlet for a biological fluid and the filter according to any of [1] to [9] contained in the housing.

Advantageous Effect of Invention

According to the present invention, a filter and a filter device for treating a biological fluid can be provided, which are capable of treating a biological fluid containing erythrocytes without adversely affecting the erythrocytes.

BRIEF DESCRIPTION OF DRAWINGS

FIG. 4 is a table showing monomer compositions, coating amounts, matrix materials, and evaluation results in Examples.

FIG. 5 is a table showing monomer compositions, coating amounts, matrix materials, and evaluation results in Comparative Examples and Reference Example.

DESCRIPTION OF EMBODIMENTS

Figure 1:
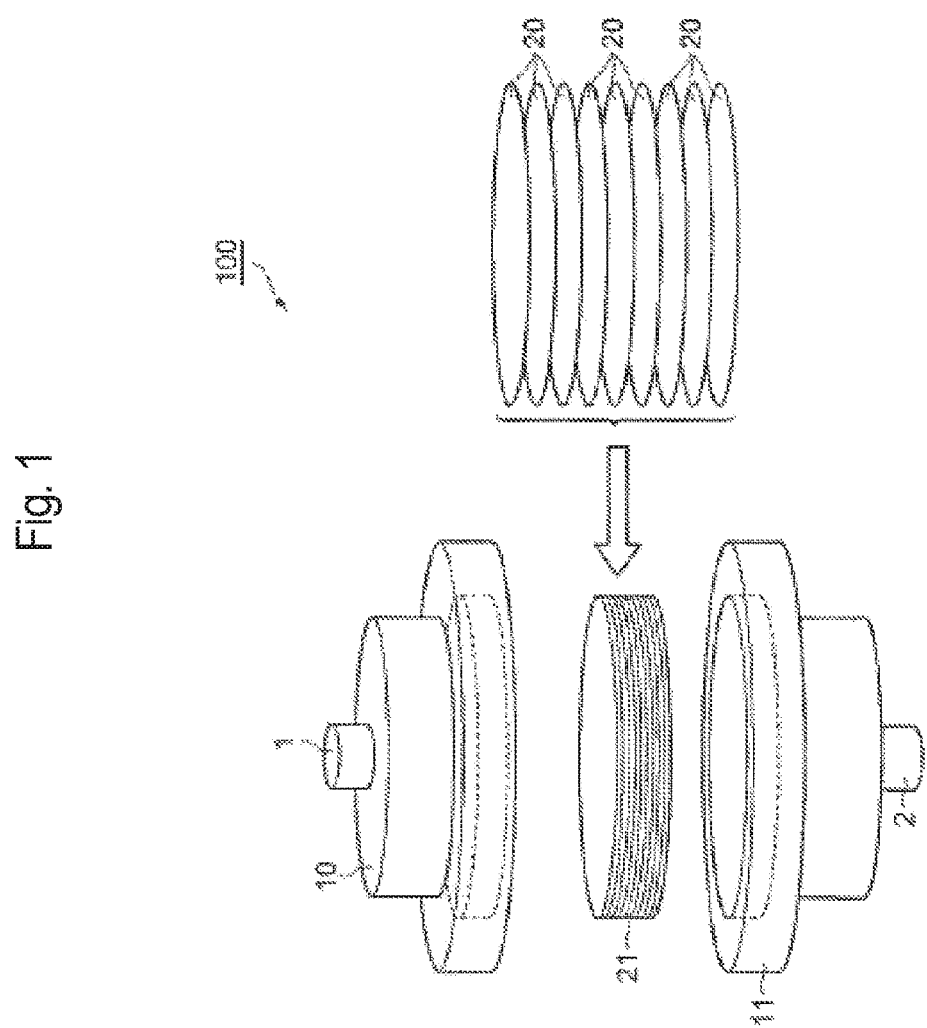
FIG. 1 is an exploded perspective view showing a filter device for treating a biological fluid according to one embodiment.

Preferred embodiments of the present invention (hereinafter referred to as "the present embodiments") will be described below in detail. The present embodiments shown below are illustrative of apparatuses and methods for implementing the technical idea of this invention and the technical idea of this invention does not specify the combination of constructional members and the like to the followings. The technical idea of this invention permits various changes to be made within the scope of claims.

The filter for treating a biological fluid containing erythrocytes according to the present embodiments comprises a matrix and a polymer retained by the matrix, and the polymer has a zwitterion-containing functional group and a basic nitrogen-containing functional group. In addition, the basic nitrogen-containing functional group is —NH₂, —NHR₁, or —NR₂R₃ (where R₁, R₂, and R₃ are alkyl groups having one to three carbon atoms).

The biological fluid containing erythrocytes is a fluid derived from a living body and encompasses all of those in which erythrocytes are dispersed, and specifically includes blood and blood products prepared from blood. The polymer is retained, for example, by being coated on the matrix. The polymer retained by the matrix is hereinafter also referred to as "coating polymer". However, the method for retaining the polymer on the matrix is not limited thereto.

(Coating Polymer)

The polymer contained in the filter according to the present embodiment contains the zwitterion-containing functional group and the basic nitrogen-containing functional group: —NH₂, —NHR₁, or —NR₂R₃ (where R₁, R₂, and R₃ are alkyl groups having one to three carbon atoms).

Examples of the zwitterion-containing functional group include functional groups represented by the following general formulas (1), (2), and (3):

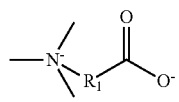

(1)

The general formula (1) represents a carbobetaine. In the general formula (1), R₁ is an alkyl group having one or more carbon atoms.

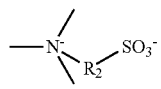

(2)

The general formula (2) represents a sulfobetaine. In the general formula (2), R₂ is an alkyl group having one or more carbon atoms.

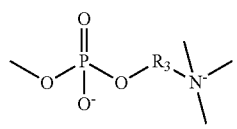

(3)

The general formula (3) represents a phosphobetaine. In general formula (3), R₃ is an alkyl group having one or more carbon atoms.

Among the zwitterion-containing functional groups represented by the general formulas (1), (2), and (3), preferred in terms of economy is a functional group derived from methyl betaine methacrylate represented by the following general formula (4).

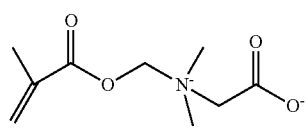

(4)

The basic nitrogen-containing functional group can be defined as a nitrogen-atom-containing functional group having the ability to receive hydrogen ion from the Bronsted-Lowry acid-base definition. Thus, it is an amino group represented by —NH₂, —NHR₁, or —NR₂R₃ (where R₁, R₂, and R₃ are alkyl groups having one to three carbon atoms), having an unshared electron pair for receiving a hydrogen ion.

Since cells, such as leukocytes, in a living body generally have a negative charge, the unshared electron pair of the basic nitrogen-containing functional group in the filter probably interact with leukocytes by having cationicity after receiving hydrogen ion, resulting in enabling the filter to remove the leukocytes. However, the presence of a functional group such as a quaternary amine showing a cation without depending on the environment such as pH in the solution makes the cationicity too strong and increases the possibility of lysing erythrocytes. Thus, the basic nitrogen-containing functional group represented by —NH₂, —NHR₁, or —NR₂R₃ is used as the functional group for imparting cationicity.

Typical examples of a compound having a basic nitrogen-containing functional group include N,N-dialkylaminoalkyl (meth)acrylates; among others, taking availability and economy into account, preferred is N,N-diethylaminoethyl (meth)acrylate.

Without being bound by the following theory, the introduction of positive and negative charges into the matrix using the zwitterion-containing functional group having the positive and negative charges in the same side chain results in no localization of a specific charge on the filter surface, and thus it is probable that the interaction between erythrocytes can be reduced and hemolysis has been capable of being decreased. It is conceivable that, by using a polymer constitutional unit containing the zwitterion-containing functional group and the basic nitrogen-containing functional group, leukocyte removal performance is enhanced with the positive charges introduced by the basic nitrogen-containing functional group. Further, it is conceivable that, by using the polymer constitutional unit containing the zwitterion-containing functional group and the basic nitrogen-containing functional group, the interaction between erythrocytes is reduced and hemolysis preventive performance is exerted by the functional groups containing the zwitterionic combination.

In view of exhibiting higher hemolysis prevention properties, the percentage of the monomer units having the zwitterion-containing functional group is preferably 1.5% or more in a molar proportion based on the whole of the monomer units which the coating polymer has. The percentage of the monomer units having the zwitterion-containing functional group based on all of the monomer units can be calculated by extracting the polymer into a solvent capable of dissolving it and combining nuclear magnetic resonance (NMR) measurement and amino group amount measurement.

The coating polymer is preferably a copolymer with a monomer capable of copolymerizing with a monomer having the nonionic group and a monomer having the basic nitrogen-containing functional group. The copolymer may be a random copolymer or a block copolymer.

Examples of the nonionic group include an alkyl group, an alkoxy group, a carbonyl group, an aldehyde group, and a phenyl group.

Typical examples of the compound having the nonionic group include alkoxyalkyl (meth)acrylates; among others, taking availability and economy into account, preferred is 2-methoxyethyl (meth)acrylate.

In the case of a filter for leukocyte removal and/or platelet removal use, it is preferable that the coating polymer consists of monomer units having the nonionic group, monomer units having the basic nitrogen-containing functional group, and monomer units having the zwitterion-containing functional group in the side chain, and do not contain monomer units other than the above units. In other words, assuming that a total of molar proportions of the monomer units constituting the coating polymer is 100, the molar proportions of the monomer units having the nonionic group (1), the monomer units having the basic nitrogen-containing functional group (m), and the monomer units having the zwitterion-containing functional group in the side chain (n) contained in the coating polymer preferably satisfy 1+m+n=100, 0<1, m, n<100. The molar proportions can be in the above range to achieve excellent leukocyte removal performance and platelet removal performance while suppressing damages, such as hemolysis, in erythrocytes. A molar proportion of the monomer units having the zwitterion-containing functional group of more than 32.5% as well as a molar proportion of the monomer units having the basic nitrogen-containing functional group of less than 1.5% tends to reduce leukocyte removal performance and platelet removal performance although a problem of hemolysis in erythrocytes does not occur. In view of exerting a higher effect of leukocyte removal and/or platelet removal while securing a hemolysis preventive effect, the molar proportion of the monomer units having the nonionic group to the monomer units having the basic nitrogen-containing functional group to the monomer units having the zwitterion-containing functional group contained in the coating polymer is, for example, 40 to 97/1.5 to 32.5/1.5 to 32.5, preferably 40 to 95/2.5 to 30/2.5 to 30, more preferably 50 to 95/2.5 to 30/2.5 to 30, still more preferably 60 to 95/2.5 to 30/2.5 to 30.

The procedures of measurement and calculation of the molar proportion of the monomer units having the nonionic group to the monomer units having the basic nitrogen-containing functional group to the monomer units having the zwitterion-containing functional group contained in the coating polymer will be described taking for example an alkoxyalkyl (meth)acrylate, an N,N-dialkylaminoalkyl (meth)acrylate, and methyl betaine methacrylate. The coating polymer is first dissolved in an appropriate solvent, such as dimethyl sulfoxide and then subjected to proton nuclear magnetic resonance ($^1$H-NMR) measurement. Based on the resultant $^1$H-NMR, the total amount of the monomer units are determined from peaks belonging to H contained in all the monomer units (a and b in the example of Example 3 to be described later). Then, from the peak belonging to H contained in an N,N-dialkylaminoalkyl (meth)acrylate (d) and the peak belonging to H contained in monomer units having a zwitterion in the side chain (i), the amount thereof is determined. In addition, using the remaining obtained by subtracting the amount of two types of the monomer units determined above from the whole amount of the monomer units as the amount of the alkoxyalkyl (meth)acrylate, the abundance proportion of the alkoxyalkyl (meth)acrylate to the N,N-dialkylaminoalkyl (meth)acrylate to methyl betaine methacrylate is calculated.

(Raw Material for Polymer)

To synthesize polymers having the zwitterion-containing functional group represented by the above formulas (1) to (3), it is preferable that the polymers are synthesized using compounds represented by the following general formulas (5), (6), and (7), respectively, as raw materials.

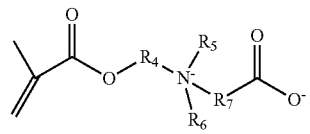

(5)

In the general formula (5), $R_5$ and $R_6$ are H or alkyl group having one to three carbon atoms; $R_4$ and $R_7$ are each independently any of $CH_2$—$CH_2$, $CH_2$—$CHR_a$, $CHR_a$—$CH_2$, $CHR_a$—$CHR_b$, $CHR_a$—$CR_bR_c$, $CR_aR_b$—$CHR_c$, $CR_aR_b$—$CR_cR_d$, and $(CH_2)_g$ (where g is an integer of 2 to 6); and $R_a$, $R_b$, $R_c$, and $R_d$ are each independently an alkyl group having one to three carbon atoms.

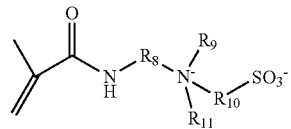

(6)

In the general formula (6), $R_9$ and $R_{11}$ are H or alkyl group having one to three carbon atoms; $R_8$ and $R_{10}$ are each independently any of $CH_2$—$CH_2$, $CH_2$—$CHR_a$, $CHR_a$—$CH_2$, $CHR_a$—$CHR_b$, $CHR_a$—$CRbR_c$, $CR_aR_b$—$CHR$, $CR_aR_b$—$CR_cR_d$, and $(CH_2)_g$ (where g is an integer of 2 to 6); and $R_a$, $R_b$, $R_e$, and $R_d$ are each independently an alkyl group having one to three carbon atoms.

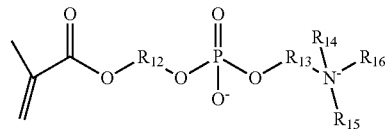

(7)

In the general formula (7), $R_{14}$, $R_{15}$, and $R_{16}$ are H or alkyl group having one to three carbon atoms; $R_{12}$ and $R_{13}$ are each independently any of $CH_2$—$CH_2$, $CH_2$—$CHR_a$, $CHR_a$—$CH_2$, $CHR_a$—$CHR_b$, $CHR_a$—$CRbR_c$, $CR_aR_b$—$CHR_c$, $CR_aR_b$—$CR_cR_d$, and $(CH_2)_g$ (where g is an integer of 2 to 6); and $R_a$, $R_b$, $R_e$, and $R_d$ are each independently an alkyl group having one to three carbon atoms.

To introduce the nonionic group into a polymer, for example, a monomer represented by the following general formula (8) is preferably used as a part of raw materials.

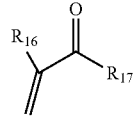

(8)-1

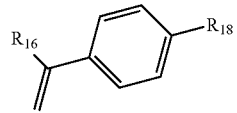

(8)-2

In the general formula (8)-1 or (8)-2, $R_{16}$ is any of H, an alkyl group having one to three carbon atoms, a phenyl group, and a derivative; $R_{17}$ is any of H, an alkyl group having one to six carbon atoms, a phenyl group, and an alkoxyalkyl group represented by —Y—O—X (where Y is an alkyl group having zero to six carbon atoms and X is H or an alkyl group having one to three carbon atoms); and $R_{18}$ is any of an alkyl group having one to three carbon atoms, an alkoxyalkyl group, a phenyl group, and a derivative thereof.

Typical examples of a monomer represented by the general formula (8) include alkoxyalkyl (meth)acrylates; among others, preferred is 2-methoxyethyl (meth)acrylate, taking availability and economy into account.

Examples of the monomer for introducing the basic nitrogen-containing functional group into the polymer include compounds represented by the following general formula (9).

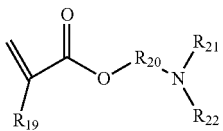
(9)

In the general formula (9), $R_{19}$, $R_{21}$, and $R_{22}$ are H or any of an alkyl group having one to three carbon atoms, a phenyl group, and a derivative thereof; $R_{20}$ is any of $CH_2$—$CH_2$, $CH_2$—$CHR_a$, $CHR_a$—$CH_2$, $CHR_a$—$CHR_b$, $CHR_a$—$CR_bR_c$, $CR_aR_b$—$CHR_c$, $CR_aR_b$—$CR_cR_d$, and $(CH_2)_e$ (where e is an integer of 2 to 6); and $R_a$, $R_b$, $R_c$, and $R_d$ are alkyl groups having one to three carbon atoms.

Typical examples of a monomer represented by the general formula (9) include N,N-dialkylaminoalkyl (meth)acrylates; among others, taking availability and economy into account, preferred is N,N-diethylaminoethyl (meth)acrylate.

(Matrix)

The material of the matrix is not particularly limited provided that it is one used as a filter for treating a biological fluid containing erythrocytes; however, the material is preferably a thermoplastic polymer. If the material of the matrix is a thermoplastic polymer, it can be spun in a molten state and thus can be made in the form of nonwoven fabric, paper, woven fabric, or mesh, for example by a melt blowing method, a flush-spinning method, a sheet-forming method. In view of such form freedom degree, the material of the matrix is more preferably polyethylene terephthalate or polybutylene terephthalate.

Examples of the form of the matrix include nonwoven fabric, paper, woven fabric, mesh, particles, and hollow fiber; among others, preferred is nonwoven fabric. The nonwoven fabric refers to a fabric-like material in which collective fibers or strings are bonded together chemically, thermally, or mechanically without being knitted or woven.

When the matrix is a nonwoven fabric or a woven fabric, the average fiber diameter can be 0.3 μm to 10 μm, preferably 0.3 μm to 3 μm, more preferably 0.5 μm to 1.8 μm. The average fiber diameter of 0.3 μm or more makes the pressure loss in filtering blood moderate. Such a diameter of 10 μm or less tends to result in the remarkable exertion of leukocyte removal performance and platelet removal performance and thus is preferred in their applications.

Here, the average fiber diameter is an average diameter measured from the photograph taken in electron microscopic observation after sampling a portion of a nonwoven fabric or a woven fabric constituting the filter.

(Filter)

In the filter, the coating polymer is retained by the matrix, and the amount thereof retained (also referred to as "coating amount") is 1.0 mg to 40 mg (both inclusive), preferably 2.0 mg to 40 mg (both inclusive), more preferably 2.5 mg to 35 mg (both inclusive), per g of the matrix. The coating amount of 1 mg or more per g of the matrix hardly causes an air block in which a portion of the filter is not used because of increasing the wettability of the filter on a biological fluid containing erythrocytes and making flowability in the filter better. In view of preventing the elution of the polymer into the biological fluid containing erythrocytes, the coating amount is preferably 40 mg or less per g of the matrix. Here, the retaining means that the coating polymer bonds or adsorbs to the matrix, for example, chemically, physically, or electrically.

The coating amount is calculated by the following procedure. The matrix before retaining the coating polymer is dried for one hour in a drier set at 60° C. and then allowed to stand in a desiccator for one hour or more, followed by measuring weight (A g). The matrix retaining the coating polymer (filter) is similarly dried for one hour in a drier at 60° C. and then allowed to stand in a desiccator for one hour or more, followed by weight (B g). The coating amount is calculated using the following calculation formula.

Coating amount (mg/g matrix)=$(B-A) \times 1000/A$

The filter according to the present embodiment can treat a biological fluid containing erythrocytes without adversely affecting the erythrocytes and thus is suitably used as a filter for a leukocyte and/or platelet removal filter device for a blood product containing erythrocytes or a filter for an extracorporeal circulation therapy filter device for removing activated leukocytes from the blood of patients. Examples of the blood product containing erythrocytes include whole blood products and erythrocyte products. In view of the above effect, the blood product containing erythrocytes is preferably a product for transfusion.

The extracorporeal circulation therapy filter device can be applied to diseases being treated provided that these diseases are diseases, one of whose causes is the excessive release of physiologically active substances by leukocyte, such as septicemia, systemic inflammatory response syndrome (SIRS), rheumatism, and ulcerative colitis.

In one embodiment of the present invention, a filter and a filter device for removing leukocytes and platelets for a blood product containing erythrocytes are provided.

(Method for Producing Filter)

The filter can be obtained by having the above matrix retain the above-described coating polymer. The retaining method, specifically the coating method, is not particularly limited; however, for example, an application method, a spraying method, and a dip method can be used.

The dip method can be carried out by dipping the matrix in a coating solution in which the coating polymer is dissolved in a suitable organic solvent, such as alcohol, chloroform, acetone, tetrahydrofuran, or dimethylformamide, then removing the excess solution, and thereafter drying the resultant using an appropriate means, such as air drying. Drying methods include a method involving air drying in a dry gas and a method involving drying at ordinary temperature or while heating in a reduced-pressure atmosphere.

The application method and the spraying method can be carried out by applying or spraying the coating solution onto the matrix and then drying the resultant as described above.

(Biological Fluid-treating Filter Device)

FIG. 1 is an exploded perspective view showing a biological fluid-treating filter device according to one embodiment. The biological fluid-treating filter device 100 shown in FIG. 1 comprises a resin-made jig 10 having an inlet 1 for a blood product containing erythrocytes and a resin-made jig 11 having an outlet 2 for the blood product, and contains a filter unit 21 in which nine filters 20 according to the present embodiment are laminated in a housing formed by the resin-made jig 10 and the resin-made jig 11. The number of filters 20 in the filter unit 21 is not particularly limited and may be properly set. The resin-made jig 10 and the resin-made jig 11 may be bonded together by fusion, adhesion with an adhesive, or the like.

Figure 2:
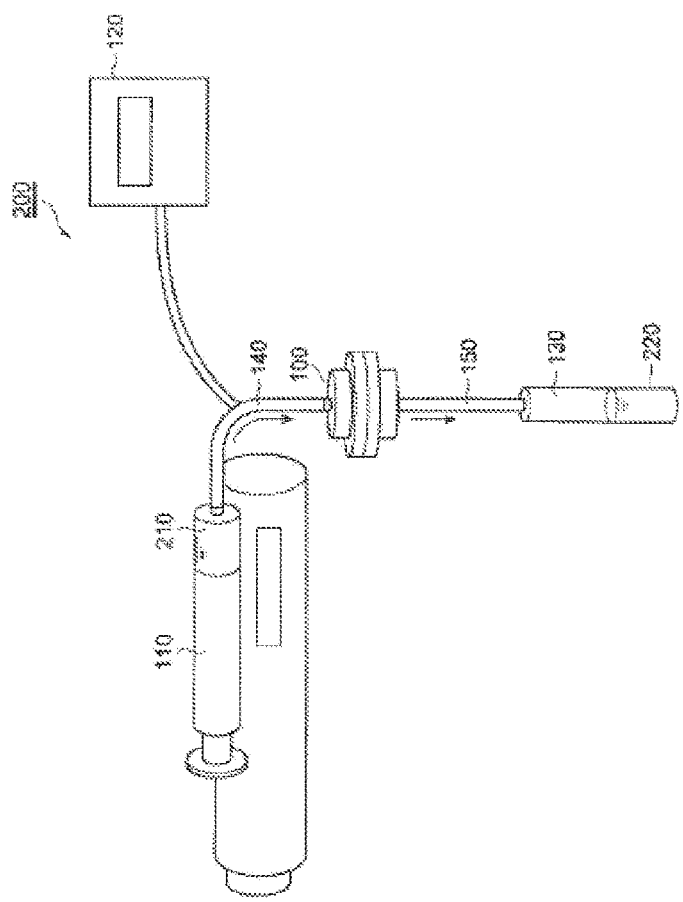
FIG. 2 is a schematic diagram showing a blood product filtration system according to one embodiment.

FIG. 2 is a schematic diagram showing a biological fluid-treating system according to one embodiment. The biological fluid-treating system 200 shown in FIG. 2 comprises a syringe pump 110 containing a pre-treatment biological fluid 210, the biological fluid-treating filter device 100, and a container 130 containing a post-treated biological fluid 220. The syringe pump 110 and the biological fluid-treating filter device 100 are connected through a tube 140. The biological fluid-treating filter device 100 and the container 130 are connected through a tube 150.

The pre-treatment biological fluid 210 transferred from the syringe pump 110 through the tube 140 is treated in the biological fluid-treating filter device 100 to remove leukocytes and platelets. Since the biological fluid-treating filter device 100 contains the above filter according to the present embodiment, no hemolysis of erythrocytes and the like occur in the post-treated biological fluid 220. The post-treated biological fluid 220 is contained in the container 130. For example, if the biological fluid is a blood product, it is used as a blood product for transfusion.

EXAMPLES

The present invention is described below in further detail based on Examples. However, the invention is not intended to be limited to the following Examples.

Example 1

(Synthesis of Coating Polymer and Measurement of Molar Proportion)

A copolymer of 2-methoxyethyl (meth)acrylate (MEMA), N,N-diethylaminoethyl (meth)acrylate (DEAEMA), and methyl betaine methacrylate (CMB) was synthesized by conventional solution polymerization. The polymerization was carried out under conditions of polymerization reaction at 60° C. for eight hours in a 1 mole/L ethanol solution of each monomer in the presence of 0.0025 mole/L azoisobutyronitrile (AIBN) as an initiator. The resultant polymer polymerization solution was added dropwise into water, and the precipitated polymer was recovered. The recovered polymer was pulverized and then dried under conditions of reduced pressure for 24 hours to provide a coating polymer.

Figure 3:
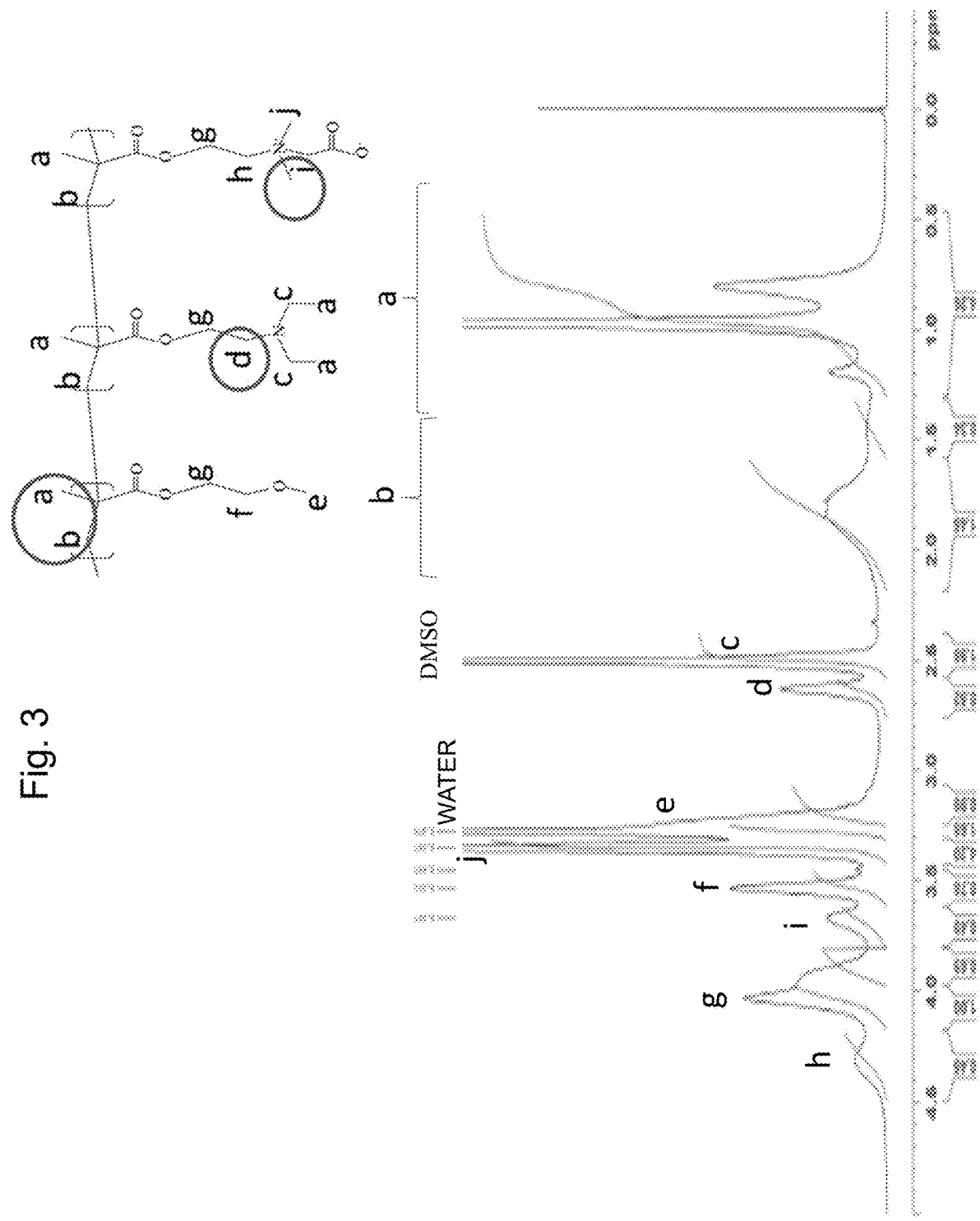
FIG. 3 is a $^1$H-NMR chart of a coating polymer according to Example 1.

The molar proportion of 2-methoxyethyl (meth)acrylate monomer to N,N-diethylaminoethyl (meth)acrylate monomer to methyl betaine methacrylate in the coating polymer was calculated by dissolving the resultant coating polymer in dimethyl sulfoxide and then subjected to $^1$H-NMR measurement. The $^1$H-NMR chart of the coating polymer and the assignment of each H atom are shown in FIG. 3. As a result of calculating the molar proportion from the H atoms of f, d, and i, the molar proportion of 2-methoxyethyl (meth)acrylate to N,N-diethylaminoethyl (meth)acrylate to methyl betaine methacrylate was 70/10/20.

(Preparation of Coating Solution)

The coating polymer was added to 90 w/w % ethyl alcohol, which was then stirred for 12 hours to prepare a coating solution having a coating polymer concentration of 0.56% by weight.

(Coating Method)

A nonwoven fabric consisting of polyethylene terephthalate (PET) fibers having an average fiber diameter of 1.2 μm (a weight of 40 g/m$^2$, "Microweb" from Asahi Kasei Fibers Corporation) was cut to a size of 210 mm×150 mm and dipped in a metal-made vat containing the coating solution for 20 seconds. The excess coating solution was removed, followed by air drying.

(Measurement of Coating Amount)

In the above coating, the coating amount was determined from the following calculation formula using the nonwoven fabric amount measured after drying the nonwoven fabric cut to 210 mm×150 mm for one hour in a hot air drier set at 60° C. (A g) and the coated nonwoven fabric amount measured after similarly drying the nonwoven fabric coated by the above method for one hour or more in a hot air drier set at 60° C. (B g).

Coating amount=(weight $B$−weight $A$)×1000/weight $A$

As a result, the coating amount per g of the matrix was found to be 20 mg.

(Leukocyte Removal Performance, Platelet Removal Performance and Hemolysis Test Method)

The coated nonwoven fabric was punched out using a 20-ϕm punching blade, and nine sheets of the resultant were laminated and held between the resin-made jigs 10 and 11 having the inlet 1 and the outlet 2, respectively for a blood product as shown in FIG. 1 to prepare a removal filter device. The removal filter device was subjected to a blood evaluation test (leukocyte removal performance, platelet removal performance and hemolysis test) using a filtration system as shown in FIG. 2. The blood product used for the blood evaluation test was CDP-added preserved human whole blood. Blood collected from a donor and preserved at room temperature for 24 hours was used. The flow rate of the blood product in the test was set at 40 mL/hour.

(Leukocyte Removal Performance)

As a result of calculating leukocyte removal performance according to the following formula for computation, the leukocyte removal performance was found to be 4.5.

Leukocyte removal performance=−log [(leukocyte concentration in post-filtered blood product)/(leukocyte concentration in pre-filtration blood product)]

The measurement of the leukocyte concentration in the blood products before and after filtration was carried out using a leukocyte count measurement kit "LeukoCOUNT" from Becton Dickinson (BD) Co., Ltd and a flow cytometer FACS Cantoll from BD Co., Ltd.

(Platelet Removal Performance)

As a result of calculating platelet removal performance according to the following calculation formula, the platelet removal performance was found to be 99%.

Platelet removal performance=[(platelet concentration in pre-filtration blood product)−(platelet concentration in post-filtration blood product)/platelet concentration in pre-filtration blood product]×100

The platelet concentration in the blood products before and after filtration was measured using an automated multi-channel blood cell counter (K-4500 from Japan Sysmex Corporation).

(Hemolysis Test Method)

The blood products before and after filtration were centrifuged at 3,000 rotations/minute (1,700×g) for 15 minutes, and then the coloration of the supernatant portions before and after filtration was observed and compared against a white paper or the like and evaluated using the following criteria. The result was no hemolysis (−).

(i) Hemolysis positive (+) when the red color of the supernatant from the blood product after filtration is definitely dark compared to that of the supernatant from the blood product before filtration.

(ii) Hemolysis positive (±) when the supernatant from the blood product after filtration is red-colored compared to the supernatant from the blood product before filtration.

(iii) Hemolysis negative (−) when the supernatant from the blood product after filtration is not red-colored compared to the supernatant from the blood product before filtration.

Example 2

A filter was used which was the same as that in Example 1 except that the coating amount of the coating polymer was 2.5 mg per g of the matrix. As a result of performing leukocyte removal performance, platelet removal performance and hemolysis evaluation in the same way as in Example 1, they were 4.4, 99%, and hemolysis negative (−), respectively.

Example 3

A filter was used which was the same as that in Example 1 except that the coating amount of the coating polymer was 30 mg per g of the matrix. As a result of performing leukocyte removal performance, platelet removal performance and hemolysis evaluation in the same way as in Example 1, they were 4.5, 99%, and hemolysis negative (−), respectively.

Example 4

A filter was used which was the same as that in Example 1 except that the material of the nonwoven fabric as a matrix was polybutylene terephthalate (PBT). As a result of performing leukocyte removal performance, platelet removal performance and hemolysis evaluation in the same way as in Example 1, they were 4.5, 99%, and hemolysis negative (−), respectively.

Example 5

A filter was used which was the same as that in Example 1 except that the composition of the coating polymer was MEMA/DEAEMA/CMB=95/2.5/2.5 (molar proportion) and that the coating amount of the coating polymer was 1.0 mg per g of the matrix. As a result of performing leukocyte removal performance, platelet removal performance and hemolysis evaluation in the same way as in Example 1, they were 4.4, 99%, and hemolysis negative (−), respectively.

Example 6

A filter was used which was the same as that in Example 1 except that the composition of the coating polymer was MEMA/DEAEMA/CMB=95/2.5/2.5 (molar proportion) and that the coating amount of the coating polymer was 2.5 mg per g of the matrix. As a result of performing leukocyte removal performance, platelet removal performance and hemolysis evaluation in the same way as in Example 1, they were 4.4, 99%, and hemolysis negative (−), respectively.

Example 7

A filter was used which was the same as that in Example 1 except that the composition of the coating polymer was MEMA/DEAEMA/CMB=67.5/30/2.5 (molar proportion) and that the coating amount of the coating polymer was 35 mg per g of the matrix. As a result of performing leukocyte removal performance, platelet removal performance and hemolysis evaluation in the same way as in Example 1, they were 4.5, 99%, and hemolysis negative (−), respectively.

Example 8

A filter was used which was the same as that in Example 1 except that the composition of the coating polymer was MEMA/DEAEMA/CMB=67.5/2.5/30 (molar proportion) and that the coating amount of the coating polymer was 1.0 mg per g of the matrix. As a result of performing leukocyte removal performance, platelet removal performance and hemolysis evaluation in the same way as in Example 1, they were 4.3, 99%, and hemolysis negative (−), respectively.

Example 9

A filter was used which was the same as that in Example 1 except that the composition of the coating polymer was methyl methacrylate (MMA)/N,N-diethylaminoethyl acrylate (DEAEA)/CMB=67.5/30/2.5 (molar proportion) and that the coating amount of the coating polymer was 20 mg per g of the matrix. As a result of performing hemolysis evaluation in the same way as in Example 1, it was hemolysis negative (−).

Example 10

A filter was used which was the same as that in Example 1 except that the composition of the coating polymer was MMA/DEAEA/methyl sulfobetaine methacrylate (SMB)=67.5/30/2.5 (molar proportion) and that the coating amount of the coating polymer was 20 mg per g of the matrix. As a result of performing hemolysis evaluation in the same way as in Example 1, it was hemolysis negative (−).

Example 11

A filter was used which was the same as that in Example 1 except that the composition of the coating polymer was MMA/DEAEA/methyl phosphobetaine methacrylate (PMB)=67.5/30/2.5 (molar proportion) and that the coating amount of the coating polymer was 20 mg per g of the matrix. As a result of performing hemolysis evaluation in the same way as in Example 1, it was hemolysis negative (−).

Comparative Example 1

A filter was used which was the same as that in Example 1 except that the composition of the coating polymer was MEMA/DEAEMA=70/30 (molar ratio) and that the coating amount of the coating polymer was 5 mg per g of the matrix. As a result of performing leukocyte removal performance, platelet removal performance and hemolysis evaluation in the same way as in Example 1, they were 4.0, 99%, and hemolysis positive (+), respectively.

Comparative Example 2

A filter was used which was the same as that in Example 1 except that the composition of the coating polymer was MEMA/DEAEMA=85/15 (molar proportion). As a result of performing leukocyte removal performance, platelet removal performance and hemolysis evaluation in the same way as in Example 1, they were 2.8, 75%, and hemolysis negative (−), respectively.

Comparative Example 3

A filter was used which was the same as that in Example 1 except that the composition of the coating polymer was MEMA/CMB=85/15 (molar proportion). As a result of performing leukocyte removal performance, platelet removal performance and hemolysis evaluation in the same way as in Example 1, they were 2.5, 60%, and hemolysis negative (−), respectively.

Comparative Example 4

A filter was used which was the same as that in Example 1 except that the composition of the coating polymer was MEMA/DEAEMA/CMB=30/35/35 (molar proportion). As a result of performing leukocyte removal performance, platelet removal performance and hemolysis evaluation in the same way as in Example 1, they were 3.5, 99%, and hemolysis positive (±), respectively.

Comparative Example 5

A filter was used which was the same as that in Example 1 except that the composition of the coating polymer was MEMA/DEAEMA/AH (acrylic acid; cationic monomer)= 60/30/10 (molar proportion) and that the coating amount of the coating polymer was 20 mg per g of the matrix. As a result of performing leukocyte removal performance, platelet removal performance and hemolysis evaluation in the same way as in Example 1, they were 3.7, 90%, and hemolysis positive (+), respectively.

Comparative Example 6

A filter was used which was the same as that in Example 1 except that the composition of the coating polymer was MEMA/DEAEMA/AH (acrylic acid; cationic monomer) =70/10/20 (molar proportion) and that the coating amount of the coating polymer was 20 mg per g of the matrix. As a result of performing leukocyte removal performance, platelet removal performance and hemolysis evaluation in the same way as in Example 1, they were 3.2, 90%, and hemolysis negative (−), respectively.

Comparative Example 7

A filter was used which was the same as that in Example 1 except that the composition of the coating polymer was MEMA/DEAEMA/DEGMEMA (diethylene glycol methoxyethyl methacrylate: nonionic monomer)=60/30/10 (molar proportion). As a result of performing leukocyte removal performance, platelet removal performance and hemolysis evaluation in the same way as in Example 1, they were 3.7, 99%, and hemolysis positive (+), respectively.

Comparative Example 8

A filter was used which was the same as that in Example 1 except that the composition of the coating polymer was MEMA/DEAEMA/DEGMEMA (nonionic monomer)=70/10/20 (molar proportion). As a result of performing leukocyte removal performance, platelet removal performance and hemolysis evaluation in the same way as in Example 1, they were 3.1, 99%, and hemolysis negative (−), respectively.

Comparative Example 9

A filter was used which was the same as that in Example 3 except that the composition of the coating polymer was MEMA/DEACMA (diethylammonium chloride methacrylate: a cationic functional group having a quaternary ammonium group)/CMB=70/10/20 (molar proportion). As a result of performing leukocyte removal performance, platelet removal performance and hemolysis evaluation in the same way as in Example 1, they were 4.4, 99%, and hemolysis positive (+), respectively.

Comparative Example 10

A filter was used which was the same as that in Example 8 except that the composition of the coating polymer was MEMA/DEACMA (diethylammonium chloride methacrylate; a cationic functional group having a quaternary ammonium group)/CMB=67.5/2.5/30 (molar proportion). As a result of performing leukocyte removal performance, platelet removal performance and hemolysis evaluation in the same way as in Example 1, they were 4.3, 99%, and hemolysis positive (+), respectively.

Reference Example 1

A filter was removed from a leukocyte removal filter device (Sepacel from Asahi Kasei Medical Co., Ltd.) and subjected to leukocyte removal performance, platelet removal performance and hemolysis evaluation in the same way as in Example 1; as a result, they were 3.0, 95%, and hemolysis negative (−), respectively.

The monomer compositions, the coating amounts, the matrix materials, and the evaluation results in Examples, Comparative Examples, and Reference Example are shown together in FIGS. 4 and 5.

The monomer having the nonionic group, the monomer having the basic nitrogen-containing functional group, and the monomer having the zwitterion-containing functional group in the side chain were contained as monomer components in the coating polymer, and their composition proportion could be controlled to treat the biological fluid containing erythrocytes without adversely affecting the erythrocytes. The filter for leukocyte and platelet removal applications could efficiently remove leukocytes and platelets.

REFERENCE SIGNS LIST

1: Inlet; 2: Outlet; 10, 11: Resin-made Jig, 20: Filter; 21: Filter Unit; 100: Biological Fluid-treating Filter Device; 110: Syringe Pump; 130: Container; 140, 150: Tube; 200:

Biological Fluid-treating System; 210: Pre-treatment Biological Fluid; and 220: Post-treated Biological Fluid.

The invention claimed is:

1. A biological fluid-treating filter for treating a biological fluid containing erythrocytes, comprising:
    a matrix, and
    a polymer retained by the matrix,
    the polymer comprising a zwitterion-containing functional group and a basic nitrogen-containing functional group, wherein the basic nitrogen-containing functional group is —$NHR_1$ or —$NR_2R_3$ where $R_1$, $R_2$, and $R_3$ are alkyl groups having one to three carbon atoms,
    the polymer further comprises a nonionic group, and the molar proportions of monomer units having the nonionic group (l), monomer units having the basic nitrogen-containing functional group (m), and monomer units having the zwitterion-containing functional group (n) satisfy the relationships:

$l+m+n=100$, $0<l,m,n<100$, where a total of molar proportions of the monomer units constituting the polymer is 100,
    wherein in the polymer, the monomer unit having the nonionic group is an alkoxyalkyl (meth)acrylate, and the monomer unit having the basic nitrogen-containing functional group is an N,N-dialkylaminoalkyl (meth)acrylate.

2. The biological fluid-treating filter according to claim 1, wherein the polymer is retained in an amount of 1.0 mg or more per gram of the matrix.

3. The biological fluid-treating filter according to claim 1, wherein the zwitterion-containing functional group is derived from at least one selected from the group consisting of carbobetaine, sulfobetaine, and phosphobetaine.

4. The biological fluid-treating filter according to claim 1, wherein the molar proportion of monomer units having the nonionic group (l) to monomer units having the basic nitrogen-containing functional group (m) to monomer units having the zwitterion-containing functional group (n) is l/m/n=40 to 97/1.5 to 32.5/1.5 to 32.5.

5. The filter according to claim 1, wherein the alkoxyalkyl (meth)acrylate is 2-methoxyethyl (meth)acrylate; the N,N-dialkylaminoalkyl (meth)acrylate is N,N-diethylaminoethyl (meth)acrylate; and the zwitterion-containing functional group is methyl betaine methacrylate.

6. The filter according to claim 1, wherein the material of the matrix is polyethylene terephthalate or polybutylene terephthalate.

7. The filter according to claim 1, wherein the matrix is a nonwoven fabric.

8. A filter device for treating a biological fluid containing erythrocytes, comprising a housing comprising an inlet and an outlet for a biological fluid and the filter according to claim 1 contained in the housing.

* * * * *